(12) United States Patent
Warner et al.

(10) Patent No.: US 10,546,146 B2
(45) Date of Patent: Jan. 28, 2020

(54) CATHETER AUTHORIZATION SYSTEM AND METHOD

(71) Applicant: General Electric Company, Schenectady, NY (US)

(72) Inventors: Adrian F. Warner, Wauwatosa, WI (US); Daniel R. Schneidewend, Wauwatosa, WI (US); Rodger F. Schmit, Wauwatosa, WI (US); Nathan Dworshak, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 234 days.

(21) Appl. No.: 15/635,605

(22) Filed: Jun. 28, 2017

(65) Prior Publication Data

US 2019/0005259 A1    Jan. 3, 2019

(51) Int. Cl.
*G06F 21/00* (2013.01)
*G06F 21/62* (2013.01)
(Continued)

(52) U.S. Cl.
CPC ............ *G06F 21/6218* (2013.01); *A61B 5/00* (2013.01); *A61B 5/0215* (2013.01); *G06F 21/83* (2013.01);
(Continued)

(58) Field of Classification Search
CPC .. G06F 21/6218; G06F 21/6245; G06F 21/31; G06F 21/32; G16H 40/63; A61B 5/00; H04Q 9/00
(Continued)

(56) References Cited

U.S. PATENT DOCUMENTS 4,720,907 A    1/1988  Raap
4,856,530 A    8/1989  Vanderveden
(Continued)

FOREIGN PATENT DOCUMENTS

AU    2009100547    3/2010
AU    2009100749    4/2010
(Continued)

OTHER PUBLICATIONS

International Search Report and Written Opinion issued in connection with corresponding PCT Application No. PCT/US2018/039907 dated Oct. 29, 2018.

*Primary Examiner* — Hosuk Song
(74) *Attorney, Agent, or Firm* — Boyle Fredrickson, S.C.

(57) ABSTRACT

In the present invention, a medical device authorization system is employed to associate software contained on a medical computing system/computer, such as an EP mapping and recording system, that pertains to a specific medical device, e.g., a catheter, connected to the computer such that the software is only utilized by the computer in conjunction with a catheter that is authorized for use with the computer. The authorization system utilizes an analog authorization waveform/signal that is mixed with the analog device/catheter measured signals transmitted to the computer. The authorization waveform distorts the measured signals in a manner that renders the signals able to be displayed by the system but unusable, unless the computer includes a signal filter operably connected to the device/catheter interface that is configured to remove the interfering authorization waveform from the measured signal.

20 Claims, 2 Drawing Sheets

(51) Int. Cl.
- *H04Q 9/00* (2006.01)
- *G16H 40/63* (2018.01)
- *A61B 5/00* (2006.01)
- *G06F 21/83* (2013.01)
- *G06F 21/85* (2013.01)
- *A61B 5/0215* (2006.01)
- *G16H 40/40* (2018.01)
- *G16H 20/40* (2018.01)

(52) U.S. Cl.
CPC ............ *G06F 21/85* (2013.01); *G16H 20/40* (2018.01); *G16H 40/40* (2018.01); *G16H 40/63* (2018.01); *H04Q 9/00* (2013.01); *A61B 2562/226* (2013.01); *A61B 2562/227* (2013.01)

(58) Field of Classification Search
USPC ..................................... 726/2–8, 16–19, 21
See application file for complete search history.

(56) References Cited

U.S. PATENT DOCUMENTS

| | | | |
|---|---|---|---|
| 5,720,293 | A | 2/1998 | Quinn et al. |
| 6,920,360 | B2 * | 7/2005 | Lee ............... A61N 1/37211 607/60 |
| 7,048,687 | B1 * | 5/2006 | Reuss ............... A61B 5/00 600/300 |
| 7,076,520 | B2 * | 7/2006 | Nelson ............ G06F 19/3418 709/203 |
| 7,823,214 | B2 | 10/2010 | Rubinstein et al. |
| 8,161,567 | B2 | 4/2012 | Rubinstein et al. |
| 8,208,853 | B2 | 6/2012 | Lydon et al. |
| 8,238,811 | B2 | 8/2012 | Lydon |
| 8,321,019 | B2 | 11/2012 | Esch et al. |
| 8,435,232 | B2 | 5/2013 | Aeby et al. |
| 8,504,823 | B2 | 8/2013 | Carpenter et al. |
| 8,509,691 | B2 | 8/2013 | Lydon et al. |
| 8,561,207 | B2 | 10/2013 | Chinn et al. |
| 8,634,761 | B2 | 1/2014 | Lydon |
| 8,696,647 | B2 | 4/2014 | Bizup et al. |
| 8,719,112 | B2 | 5/2014 | Carpenter et al. |
| 8,719,603 | B2 | 5/2014 | Belesiu et al. |
| 8,763,079 | B2 | 6/2014 | Rubinstein et al. |
| 8,925,069 | B2 | 12/2014 | Louboutin et al. |
| 8,935,774 | B2 | 1/2015 | Belesiu et al. |
| 9,071,441 | B2 | 6/2015 | Ross et al. |
| 9,124,434 | B2 | 9/2015 | Krishnamurthy et al. |
| 9,141,780 | B2 | 9/2015 | Subramaniam et al. |
| 9,223,958 | B2 | 12/2015 | Rubinstein et al. |
| 9,563,766 | B2 | 2/2017 | Lim et al. |
| 9,594,415 | B2 | 3/2017 | Obie et al. |
| 2006/0156415 | A1 | 7/2006 | Rubinstein et al. |
| 2008/0056540 | A1 * | 3/2008 | Vadodaria .......... G16H 40/63 382/115 |
| 2008/0255504 | A1 | 10/2008 | Nekich et al. |
| 2009/0083834 | A1 | 3/2009 | Rubinstein et al. |
| 2010/0075604 | A1 | 3/2010 | Lydon et al. |
| 2010/0173673 | A1 | 7/2010 | Lydon |
| 2011/0061113 | A1 | 3/2011 | Rubinstein et al. |
| 2011/0125601 | A1 | 5/2011 | Carpenter et al. |
| 2011/0126005 | A1 | 5/2011 | Carpenter et al. |
| 2011/0167262 | A1 | 7/2011 | Ross et al. |
| 2012/0047368 | A1 | 2/2012 | Chinn et al. |
| 2012/0272297 | A1 | 10/2012 | Lydon |
| 2012/0278882 | A1 | 11/2012 | Lydon et al. |
| 2012/0304266 | A1 | 11/2012 | Subramaniam et al. |
| 2013/0030482 | A1 | 1/2013 | Warner et al. |
| 2013/0232350 | A1 | 9/2013 | Belesiu et al. |
| 2013/0232571 | A1 | 9/2013 | Belesiu et al. |
| 2014/0208416 | A1 | 7/2014 | Lydon |
| 2014/0223174 | A1 | 8/2014 | Krishnamurthy et al. |
| 2014/0229326 | A1 | 8/2014 | Carpenter et al. |
| 2015/0082049 | A1 | 3/2015 | Rubinstein et al. |
| 2015/0089248 | A1 | 3/2015 | Obie et al. |
| 2015/0317473 | A1 | 11/2015 | Lim et al. |
| 2015/0342564 | A1 | 12/2015 | Hossack et al. |
| 2015/0358169 | A1 | 12/2015 | Krishnamurthy et al. |
| 2016/0088476 | A1 | 3/2016 | Park et al. |
| 2016/0110536 | A1 | 4/2016 | Rubinstein et al. |
| 2016/0184025 | A1 | 6/2016 | Warner et al. |
| 2016/0184028 | A1 | 6/2016 | Warner et al. |

FOREIGN PATENT DOCUMENTS

| | | |
|---|---|---|
| AU | 2009100750 | 4/2010 |
| AU | 2011100222 | 3/2011 |
| AU | 2010292318 | 5/2013 |
| AU | 2011240960 | 6/2014 |
| AU | 2013203800 | 2/2015 |
| AU | 2014323428 | 2/2016 |
| CA | 1200852 | 2/1986 |
| CA | 2148714 | 12/2006 |
| CA | 2793617 | 10/2011 |
| CA | 2922505 | 3/2015 |
| CA | 2591164 | 6/2017 |
| CN | 101099157 | 1/2012 |
| CN | 102708319 | 10/2012 |
| CN | 102845046 | 12/2012 |
| CN | 102983970 | 3/2013 |
| CN | 101699458 | 5/2013 |
| CN | 103682898 | 3/2014 |
| CN | 104077622 | 10/2014 |
| CN | 104160406 | 11/2014 |
| CN | 104641378 | 5/2015 |
| CN | 102483787 | 7/2015 |
| CN | 105046142 | 11/2015 |
| CN | 105190638 | 12/2015 |
| CN | 105308925 | 2/2016 |
| CN | 105683861 | 6/2016 |
| CN | 105704113 | 6/2016 |
| CN | 106105150 | 11/2016 |
| CN | 106330859 | 1/2017 |
| CN | 106464395 | 2/2017 |
| CN | 106464611 | 2/2017 |
| EP | 1834273 | 9/2007 |
| EP | 2324443 | 5/2011 |
| EP | 2476078 | 7/2012 |
| EP | 2559225 | 2/2013 |
| EP | 2823433 | 1/2015 |
| EP | 2951976 | 12/2015 |
| EP | 3032449 | 6/2016 |
| EP | 3047347 | 7/2016 |
| GB | 2466328 | 6/2010 |
| GB | 2473544 | 3/2011 |
| IN | 201101411 | 1/2012 |
| IN | 201202211 | 5/2013 |
| IN | 201208117 | 12/2015 |
| IN | 201647004799 | 8/2016 |
| JP | 2010183571 | 8/2010 |
| JP | 04571677 | 10/2010 |
| JP | 04917108 | 4/2012 |
| JP | 04981887 | 7/2012 |
| JP | 2014053966 | 3/2014 |
| JP | 05786013 | 9/2015 |
| JP | 05856146 | 2/2016 |
| KR | 2007104393 | 10/2007 |
| KR | 2008113381 | 12/2008 |
| KR | 2009027777 | 3/2009 |
| KR | 1019884 | 3/2011 |
| KR | 2012102783 | 9/2012 |
| KR | 2012104519 | 9/2012 |
| KR | 2013050268 | 5/2013 |
| KR | 2013061089 | 6/2013 |
| KR | 2013073872 | 7/2013 |
| KR | 1396756 | 5/2014 |
| KR | 2014063549 | 5/2014 |
| KR | 1412425 | 6/2014 |
| KR | 1439639 | 9/2014 |
| KR | 2015036765 | 4/2015 |
| KR | 1522628 | 5/2015 |
| KR | 1535017 | 7/2015 |
| KR | 2016035427 | 3/2016 |
| KR | 1644280 | 7/2016 |
| WO | 2006073702 | 7/2006 |

(56) References Cited

FOREIGN PATENT DOCUMENTS

| | | |
|---|---|---|
| WO | 2010027694 | 3/2010 |
| WO | 2011031760 | 3/2011 |
| WO | 2011082073 | 7/2011 |
| WO | 2011130026 | 10/2011 |
| WO | 2013134438 | 9/2013 |
| WO | 2014120695 | 8/2014 |
| WO | 2015042329 | 3/2015 |
| WO | 2016/083379 A1 | 6/2016 |

* cited by examiner

CATHETER AUTHORIZATION SYSTEM AND METHOD

BACKGROUND OF INVENTION

The invention relates generally to catheters, and more particularly to catheters including authorization systems that enable the catheters to be specifically authorized for use with a hemodynamic (HEMO), electrophysiological (EP) or other recording or mapping device or system to which the catheters are connected during studies or monitoring of patients.

Catheters are used in an increasing number of medical procedures to evaluate various conditions of the patient with which the catheter is utilized. As a result, there are many different configurations of catheters that are constructed for use in the procedures.

While many different configurations of catheters can be utilized for a particular procedure, the exact configuration of the catheter in use must be authorized by the recording or mapping device to which the catheter is connected in order for the device to correctly receive or transmit signals in the procedure using the selected catheter. This is due in large part to the nature of the signals being obtained by the catheter and transmitted to the HEMO/EP system/computer system/computing device, as the catheter necessarily needs to be properly associated or authorized for use not only to obtain the desired signals but to transmit the signals to the computer in a usable manner.

Currently, catheter and device manufacturers, increasingly want to associate proprietary algorithms and methods including those algorithms to their clinical devices to add value and differentiate from the competition. One way currently employed to do this is to digitize the signals at the catheter and to stream the digitized data into a standard digital interface on the HEMO/EP system or computer, such as through universal serial bus (USB) port on the HEMO/EP system. However, this creates problems when the device data needs to be referenced or recorded with other common signals acquired by the same HEMO/EP system and/or computer host, but through a separate and distinct digitization system than is stored and utilized on the catheter. More particularly, in this situation it is often the case that the signals from the catheter and from the other device connected to the computer are not recorded in synchronicity and thus their respective time domains are out of phase with one another. As a result, any events in the recorded signal(s) may not appear, appear time shifted, or only partially appear as a result of the time domain errors when displaying, or using the data to correlate precise events. Worse, if any algorithm utilized within the computing device/computer/EP/HEMO system requires data from outside of its own digitization domain then the phase error between the two digitization systems becomes compounded with the signal processing. This can produce significant variance in results, or in extreme cases error in the end result depending on the complexity of the algorithm(s) utilized in the signal processing and dependencies on the associated data being processed.

If signal digitization algorithms are instead present or loaded on the HEMO/EP system/computer system, and the incoming signals from the catheters are digitized through existing standard interfaces on the HEMO/EP/computer system, there is nothing in the computer system that will prevent reuse or misuse of these proprietary algorithms by end users. For example, in this system configuration virtually any competitive catheter/device technology can be interfaced with and utilize the digitization algorithms loaded onto the system. Thus, a competitor may design a catheter system that utilizes these embedded algorithms without having to independently develop suitable algorithms thereby benefitting from the computer system developer's intellectual property through the lack of controlled enablement with the developed computer system.

In addition, separate from the development of the catheters themselves, a customer may utilize the catheter with a HEMO/EP/computer system that is not compatible with the catheter, creating a misuse scenario whereby the signals from the catheter are processed with inappropriate algorithms, filtering, and preprocessing in the HEMO/EP/computer device such that the intended use, and expected results breach the original regulatory qualification.

In the prior art, one alternative solution to provide proper association of the catheter to an EP/computer system, one solution has been to require the entry into the EP/computer system of a serial number or other identifying information regarding the catheter. The identifying information can be entered automatically upon connection of the catheter to the system, such as via passive means or active digital identification chips present on or within the catheter, or can be input manually. In doing so, the EP/computer system can reference an internal listing of compatible catheters in order to determine if the catheter should be enabled for use with the EP/computer system. Examples of systems of these types are disclosed in CA Patent Nos. 1,200,852 and 2148714 and US Patent Application Publication No. US 2016/0184025, each of which are expressly incorporated herein by reference for all purposes.

However, with these solutions where the identification information can be entered manually, the system can be circumvented to enable unauthorized catheters to be used with the EP/computer system, and where the system automatically retrieves the identification information from the catheter, the system requires costly internal alterations, including custom hardware to communicate with the internal identification components within the catheter.

Accordingly, it is desirable to develop a system for the association and authorization of a catheter for use with an EP/computer system to which the catheter is connected for use in a medical procedure. The system should allow for authorization of the catheter without the need for digitization of the signal at the catheter in order to enable appropriate signal processing at the EP/computer system automatically on connection of the catheter to the system.

BRIEF DESCRIPTION OF THE INVENTION

There is a need or desire for a system to authorize a catheter for utilization with a recording or mapping system to which the catheter has been connected. The above-mentioned drawbacks and needs are addressed by the embodiments described herein in the following description.

According to one exemplary aspect of the invention, a medical device authorization system is employed to associate software contained on a medical computing system/computer, such as an EP mapping and recording system, that pertains to a specific medical device, e.g., a catheter, connected to the computing system such that the software is only utilized by the computing system in conjunction with a catheter that is authorized for use with the computing system. The authorization system utilizes an analog authorization waveform/signal that is mixed with the analog device/catheter measured signals transmitted to the computing system. The authorization waveform distorts the measured signals in a manner that renders the signals able to be displayed by the system but unusable, thereby preventing the catheter from being used in conjunction with non-approved computing system algorithms. If the device/catheter is connected to a computing system that the device/catheter is authorized for use with, the computing system includes a signal filter operably connected to the device/catheter interface that can remove the authorization waveform from the catheter measured signal. Thus, the authorization system enables the catheter and computing device to be connected utilizing the analog signal, without the need for digitization of the signal, but the authorization waveform combined with the catheter signal will limit functionality to unauthorized and unauthenticated end user computing systems.

According to another exemplary embodiment of the invention, the authorization system includes a device/catheter identification function, in which identifying information about the particular device/catheter is manually or automatically entered into the computing device upon connection of the catheter to the computing device. Entry of the device/catheter identifying information provides an initial verification of the authorization of the catheter for use with the software/algorithms on the computing system prior to the removal of the authorization waveform from the measured signal from the device. Further, the entry of the catheter identifying information can optionally be utilized as an activation of the filter within the computing device that removes the authorization waveform from the catheter signal.

According to still another exemplary aspect of the invention, the authorization system can be implemented in a number of physical manners to accommodate new and existing catheter constructions, such as in the catheter, the catheter cable, or in a catheter interface block or input module. In particular, the authorization system can be disposed in part directly in the catheter cable connector when the catheter is manufactured, as the catheter authorization system is low-tech, low cost, and easy for device manufacturers to implement. Additionally, the authorization system components can optionally be disposed in part within the adaptor cable used to connect the catheter to the recorder or mapping system catheter interface blocks. Further, the authorization system can be positioned in part within a custom catheter interface adaptor block on the recorder, and to provide interface indicator blocks, such as those disclosed in US Patent Application Publication No. 2008/0255504, which is expressly incorporated herein by reference in its entirety.

According to another aspect of the invention, a method of authorizing a device connected to an EP system for operation with the EP system includes providing an EP system including a computer having a device interface, a device connected to the interface and including a signal circuit disposed within the device for obtaining and transmitting a measured signal to be analyzed and a device authorization system within the device, the authorization system comprising a function generator operably connected to the signal circuit to produce an authorization signal related to a unique identifying characteristic of the device that is combined with the measured signal to form a combined signal and a filter disposed within the EP system capable of removing the authorization signal from the combined signal to retrieve the measured signal, connecting the device to the interface, outputting an authorization signal from the function generator, wherein the authorization signal is related to a unique identifying characteristic of the device, combining the authorization signal with the measured signal to form a combined signal, transmitting the combined signal to the EP system and filtering the authorization signal from the combined signal.

According to a further aspect of the invention, a device authorization system for enabling operation of the device with an electrophysiology (EP) recording or mapping system, including a device operably connectable to the EP system, a signal circuit disposed within the device for obtaining and transmitting a measured signal to be analyzed, a function generator operably connected to the signal circuit to produce an authorization signal related to a unique identifying characteristic of the device that is combined with the measured signal to form a combined signal and a filter disposed within the EP system capable of removing the authorization signal from the combined signal to retrieve the measured signal.

According to still another aspect of the invention, an EP system for obtaining and recording information on a patient connected to the EP system includes an amplifier including a device interface, a computer operably connected to the amplifier, a device connected to the interface and including a signal circuit disposed within the device for obtaining and transmitting a measured signal to be analyzed and a device authorization system within the device, the identification system having a function generator operably connected to the signal circuit to produce an authorization signal related to a unique identifying characteristic of the device that is combined with the measured signal to form a combined signal and a filter disposed within the EP system capable of removing the authorization signal from the combined signal to retrieve the measured signal.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
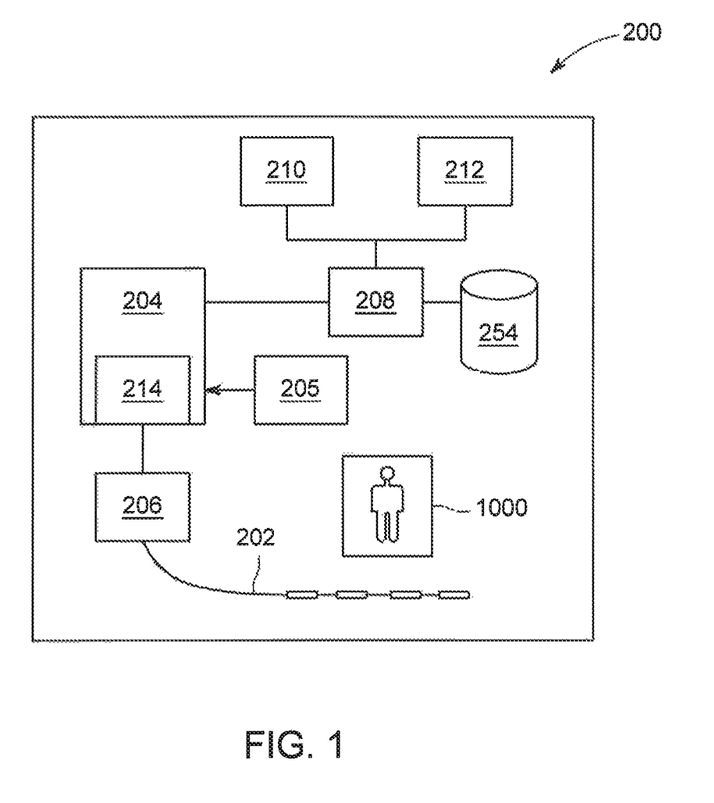
FIG. 1 is a schematic representation of an EP recording system including a catheter identification system according to one exemplary embodiment of the present invention.

FIG. 1 illustrates one exemplary embodiment of a hemodynamic (HEMO) or an electrophysiology (EP) mapping or a HEMO/EP recorder system 200, such as those used in intracardiac electrocardiography (ECG) studies within the body of a patient 1000. These systems 200 apply an electrical signal (e.g., electrical current) via one or more devices or catheters 202 to various locations of the body of the patient 1000, such as the heart. The system 200 can be similar to that disclosed in US Patent Application Publication No. US2013/0030482, which is expressly incorporated herein in its entirety. In certain embodiments, the systems 200 includes an amplifier 204 that is operably connected between a signal generator 206 and a suitable computer, controller or central processing unit (CPU) 208 where signals generated by the signal generator 206 are transmitted to the catheter 202 through the amplifier 204. A return signal from the patient 1000, such as an ECG signal, is received by the amplifier 204 either via the catheter 202 or another catheter or device 205, and is processed by the amplifier 204 prior to transmitting the return signal to the CPU 208. The CPU 208 performs additional functions on the return signal, which can be stored in database 258 and displays the information provided by the return signal on one or both of a real-time display 210 and a review display 212. The amplifier 204 also includes a catheter interface 214 that is used to connect the catheter 202 to the amplifier 204 for use with the recording or mapping system 200.

Figure 2:
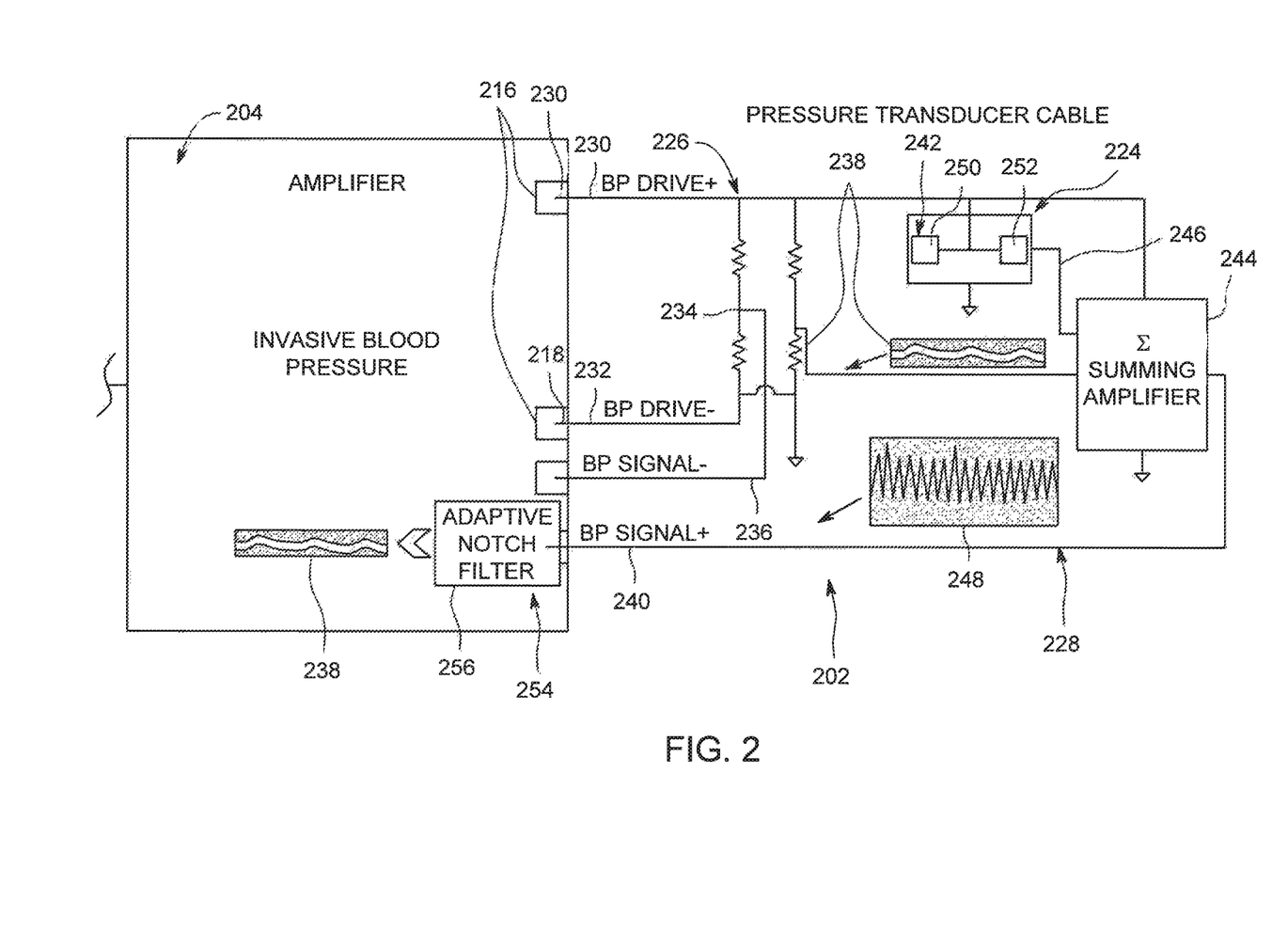
FIG. 2 is a schematic representation of the catheter authorization system for the recording system of FIG. 1 according to an exemplary embodiment of the invention.

In FIG. 2, one exemplary embodiment of a catheter interface 214 is illustrated. The interface 214 includes a number of pole sockets 216 that are configured to receive corresponding pins 218 disposed on the catheter 202 in order for the catheter 202 to be electrically coupled to the interface 214, and thus enable electric signals to pass between the interface 214 and the catheter 202. The pole sockets 216 are each connected to a catheter signal analog-to-digital converter (ADC) circuit (not shown) within the amplifier 204 in order to convert the analog signals from the pins 218 into digital signals that can be output from the ADC circuit to the CPU 208.

The interface 214 additionally includes a device/catheter authorization system 224. The authorization system 224 is formed in the illustrated exemplary embodiment within the signal circuit 226 of the device/catheter 202, which takes the form of a pressure transducer 228. The circuit 226 includes a positive drive lead 230 and a corresponding negative drive lead 232 that each receives a signal current from the amplifier 204 via the interface 214. The signals from the positive drive lead 230 and negative drive lead 232 are combined in order to negate the potential of each signal and form a driven reference signal 234 that is conducted to negative signal lead 236. This driven reference signal 234 can be compared in a known manner with the measured signal 238 obtained by the electrode(s) (not shown) on the catheter 202 that generates the measured/pressure signal 238 is and transmitted to the positive signal lead 240 in order to provide an analog signal representative of the blood pressure of the patient 1000.

Within the signal circuit 226 for the catheter 202 is also disposed a function generator 242. The function generator 242 can be digitally controlled and is operably connected to the positive drive lead 230 and to a summing amplifier 244. The function generator 242 can be formed from a computer, central processing unit or processor, or as in the illustrated exemplary embodiment can be formed as a circuit programmed to produce a constant frequency signal that is generated by the function generator 242 utilizing a unique identifying characteristic of the catheter 202 or pressure transducer 228, such as a serial number of the catheter 202, among other suitable characteristics. Utilizing this characteristic, the function generator 242 outputs an analog interference or authorization signal 246 unique to the individual catheter 202 that is mixed or combined with the measured/pressure signal 238 in the summing amplifier 244 to form a combined signal 248. This combined signal 248 is then transmitted to the positive signal lead 240 and to the interface 214.

The construction and operation of the function generator 242 can be selected from any suitable configuration, but in one exemplary embodiment the function generator 242 includes a frequency oscillator 250 that outputs a sine wave from the oscillator 250 when the catheter 202 is connected to the interface 214 for the amplifier 204. This sine wave output frequency is tuned by tuning device 252, such as capacitor or a resistor, that operates to alter the frequency of the sine wave to form the unique analog authorization signal 246 that is ultimately output to the summing amplifier 244. In one exemplary embodiment this is accomplished by altering the configuration of the tuning device 252, i.e., the capacitor or the resistor, such as by laser trimming the capacitor/resistor in accordance with the unique identifying characteristic of the catheter 202. In one exemplary embodiment, the capacitor/resistor is configured by laser trimming the capacitor/resistor utilizing a one way hash of the catheter serial number to generate a unique numberic value that can only be discovered by a system 200 that has the serial number, which is printed on the catheter 202, and the hash function and seed value which are subsequently provided via some secure method to the manufacturer of the amplifier 204 for storage therein through some method like a web lookup or a hardware key or binary software modules to maintain the secrecy of the information. In this manner, the capacitor/resistor is provided with a profile unique to the particular catheter 202 including the capacitor/resistor, thus altering the sine wave from the oscillator 250 to produce the unique analog authorization signal 246. As the authorization signal 246 is analog it can be acquired and displayed on any equipment suitably equipped to acquire such a signal via a catheter 202 or similar device. The interference or noise provided by the authorization signal 246 can be as complex as deemed necessary and in addition to a continuous sinusoid or known frequency, the authorization signal 246 can include a different form factor or be a repetitive pulse train or some other signal form wherein it is obvious to the user that the catheter 202 is not connected to the right equipment 208 when displayed by the computer 208.

To enable the authorization signal 246 to reach the interface 214 and amplifier 204, the authorization signal 246 is configured to be a signal with a frequency within the normal range for the pressure signal 238 to be obtained by the catheter 202. Within this range, the authorization signal 246 will not be eliminated from the combined signal 248 upon reaching the amplifier 204. In one exemplary embodiment the oscillator 250 is set at frequency that does not comply with any standard filter arrangement for the amplifier 204 and/or computer 208 to which the catheter 202 is connected. For example, for an ECG equipment/system 200 it would not make sense to select 50 or 60 Hz for the authorization signal 246 as notch filters are provided to remove such interference/noise. Nor should the authorization signal 246 be selected to be outside the normal signal acquisition bandwidth for the particular computing system 208, as the authorization signal 246 will be eliminated by anti-aliasing filters (not shown). In certain exemplary embodiments the authorization signal 246 can have a frequency of 1 Hz to 100 Hz—as adjusted by the resistor 252.

Upon reaching the interface 214 and amplifier 204, the combined signal 248 passes through a filter 254, which in the illustrated exemplary embodiment is a software adaptive notch filter 256. This filter 254 is a subtractive filter that is tuned exactly to the particular authorization signal frequency using the information provided to the amplifier 204/CPU 208 via tha hash function/seed value and thus removes the obfustacting authorization signal 246 reguardless of amplilitude and does not intruduct normal filter artifacts such as phase distortion, which can optionally be stored in database 258. The notch filter 256 is employed/utilized by the computer 208 and/or amplifier 204 during analysis of the combined signal 248 to remove the authorization signal 246 from the combined signal 248, leaving only the pressure signal 238 for analysis and display by the computer 208 and system 200.

In one exemplary embodiment, in order to remove the authorization signal 246 from the combined signal 248, in one exemplary embodiment the computer 208 is supplied with an authorization key in the form of encoded serialized identification or information on the particular catheter 202, such as by wireless delivery in digital media or from a secure internet service. In other exemplary embodiments, the authorization key/catheter information provided to the computer 208 can be in the form of an embedded memory device, logic circuit or other solid state design that is required to be read into the computer 208 when the catheter 202 is attached to the system 200, or a passive indicator used to provide basic family identification, such as that disclosed in US Patent Application Publication No. 2016/0184025, entitled Passive Catheter Identification And Self-Configuration System, which is hereby expressly incorporated by reference herein for all purposes. Other non-embedded identification schemes that may be employed to supply the identification information to the computer 208 include, but are not limited to RFID or bar-code entry of the information, or simply having the user type in a one-time use code number using a manual input device (not shown), such as a keyboard operably connected to the computer 208. Once entered, the computer 208 can verify the authenticity of the information provided on the catheter 202. In this verification process, the computer 208 can determine the exact frequency of the authorization signal 246 generated by the function generator 250 in the catheter 202 using the information provided on the catheter 202. The computer 208 can then tune or adjust the operation of the adaptive notch filter 256 to this exact frequency, thus enabling the filter 256 to remove only the authorization signal 246 form the combined signal 248 reaching the filter 256.

In this embodiment, the two-layer protection requires that the end user be approved to use the device, thus being able to provide the identification information to the system 200, and enabling the computer 208 and system 200 to load and execute the required software and algorithms, such as optionally stored in database 258, to both decode the signal and enable the clinical algorithms and workflow components to function. In addition, the device/catheter 202 must be approved for use with the system 200, by the ability of the system 200 to decode or appropriately filter the combined signal 248 to remove the authorization signal 246. Failure of confirmation of authorization in either layer results in no functional operation for the catheter 202 with the system 200. In this way the manufacturer of the device can assure exact matching between device, algorithms and authorized platforms that support this technology.

With regard to the catheter authorization system 224, some of the technical advantages that are provided include:
 easier to integrate into an existing acquisition and computing system;
 ensures third party algorithms are protected and available only on authorized devices;
 allows easy integration into the existing analog signal domain with 3rd party manufacturers;
 lock and authentication mechanisms provide robust protection from misuse;
 allows the recording system manufacturer to more easily integrate third party technology and algorithms into their platform;
 ensures that the signal acquisition of the protected device remains coherent within the one acquisition time domain by avoiding the need for a separate, unsynchronized digitation process; and
 ensures uniform accuracy and tolerance of all acquired signals.

In addition the device/catheter authorization system 224 also provides certain commercial advantages, including but not limited to:
 protects catheter/device manufacturer IP from unintentional or intentional misuse;
 prevents third party connection to unauthorized algorithmic processing;
 prevents the catheter/device from being used with a non-approved third party solution;
 can ensure that the catheter/device may only be purchased direct from the manufacturer by control of the authentication key or a portion thereof;
 can prevent reuse of the one-time use device;
 assures field integrity of catheter/device eliminating misuse complaints by the protections on both the catheter/device and the algorithms developed for their use.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A device authorization system for enabling operation of the device with an electrophysiology (EP) recording or mapping system, the authorization system comprising:
 a device operably connectable to the EP system;
 a signal circuit disposed within the device for obtaining and transmitting a measured signal to be analyzed;
 a function generator operably connected to the signal circuit to produce an authorization signal related to a unique identifying characteristic of the device that is combined with the measured signal to form a combined signal;
 a filter disposed within the EP system capable of removing the authorization signal from the combined signal to retrieve the measured signal.

2. A device authorization system for enabling operation of the device with an electrophysiology (EP) recording or mapping system, the authorization system comprising:
 a device operably connectable to the EP system;
 a signal circuit disposed within the device for obtaining and transmitting a measured signal to be analyzed;
 a function generator operably connected to the signal circuit to produce an authorization signal related to a unique identifying characteristic of the device that is combined with the measured signal to form a combined signal;

a filter disposed within the EP system capable of removing the authorization signal from the combined signal to retrieve the measured signal, wherein the function generator comprises:

an oscillator for generating a constant frequency authorization signal; and a tuning device configured to modify the authorization signal in a manner relative to the unique identifying characteristic of the device.

3. The device authorization system of claim 2 wherein the tuning device comprises a resistor configured using the unique identifying feature of the device.

4. The device authorization system of claim 3 wherein the resistor is configured by laser trimming the resistor utilizing the unique identifying feature of the device.

5. The device authorization system of claim 4 wherein the unique identifying feature of the device is a serial number of the device.

6. The device authorization system of claim 2 wherein the tuning device comprises a capacitor configured utilizing the unique identifying feature of the device.

7. The device authorization system of claim 2 further comprising a summing amplifier disposed between the function generator and the measured signal.

8. The device authorization system of claim 2 wherein the filter is an adaptive notch filter.

9. The device authorization system of claim 2 wherein the authorization signal has a frequency within a normal range for the measured signal.

10. The device authorization system of claim 9 wherein the authorization signal has a frequency of between 1 Hz-100 Hz.

11. A device authorization system for enabling operation of the device with an electrophysiology (EP) recording or mapping system, the authorization system comprising;

a device operably connectable to the EP system;

a signal circuit disposed within the device for obtaining and transmitting a measured signal to be analyzed;

a function generator operably connected to the signal circuit to produce an authorization signal related to a unique identifying characteristic of the device that is combined with the measured signal to form a combined signal;

a filter disposed within the EP system capable of removing the authorization signal from the combined signal to retrieve the measured signal, further comprising an authorization key that is provided to the EP system to enable operation of the filter to remove the authorization signal.

12. The device authorization system of claim 11 wherein the authorization key utilizes the unique identifying characteristic of the device.

13. The device authorization system of claim 11 wherein the authorization key is separate from the device.

14. The device authorization system of claim 2 wherein the authorization signal is an analog signal.

15. An EP system for obtaining and recording information on a patient connected to the EP system, the EP system comprising:

an amplifier including a device interface;

a computer operably connected to the amplifier;

a device connected to the interface and including a signal circuit disposed within the device for obtaining and transmitting a measured signal to be analyzed; and a device authorization system within the device, the device authorization system comprising:

a function generator operably connected to the signal circuit to produce an authorization signal related to a unique identifying characteristic of the device that is combined with the measured signal to form a combined signal; and a filter disposed within the EP system capable of removing the authorization signal from the combined signal to retrieve the measured signal.

16. An EP system for obtaining and recording information on a patient connected to the EP system, the EP system comprising:

an amplifier including a device interface;

a computer operably connected to the amplifier;

a device connected to the interface and including a signal circuit disposed within the device for obtaining and transmitting a measured signal to be analyzed; and a device authorization system within the device, the identification system comprising:

a function generator operably connected to the signal circuit to produce an authorization signal related to a unique identifying characteristic of the device that is combined with the measured signal to form a combined signal; and a filter disposed within the EP system capable of removing the authorization signal from the combined signal to retrieve the measured signal, wherein the device authorization system further comprises an authorization key provided to the EP system to enable operation of the filter to remove the authorization signal.

17. A method of authorizing a device connected to an EP system for operation with the EP system, the method comprising the steps of:

providing an EP system including a computer having a device interface, a device connected to the interface and including a signal circuit disposed within the device for obtaining and transmitting a measured signal to be analyzed and a device authorization system within the device, the authorization system comprising a function generator operably connected to the signal circuit to produce an authorization signal related to a unique identifying characteristic of the device that is combined with the measured signal to form a combined signal and a filter disposed within the EP system capable of removing the authorization signal from the combined signal to retrieve the measured signal;

connecting the device to the interface;

outputting an authorization signal from the function generator, wherein the authorization signal is related to a unique identifying characteristic of the device;

combining the authorization signal with the measured signal to form a combined signal;

transmitting the combined signal to the EP system; and filtering the authorization signal from the combined signal.

18. A method of authorizing a device connected to an EP system for operation with the EP system, the method comprising the steps of:

providing an EP system including a computer having a device interface, a device connected to the interface and including a signal circuit disposed within the device for obtaining and transmitting a measured signal to be analyzed and a device authorization system within the device, the authorization system comprising a function generator operably connected to the signal circuit to produce an authorization signal related to a unique identifying characteristic of the device that is combined with the measured signal to form a combined signal and a filter disposed within the EP system capable of removing the authorization signal from the combined signal to retrieve the measured signal;

connecting the device to the interface;

outputting an authorization signal from the function generator, wherein the authorization signal is related to a unique identifying characteristic of the device;

combining the authorization signal with the measured signal to form a combined signal;

transmitting the combined signal to the EP system; and filtering the authorization signal from the combined signal, wherein the step of filtering the authorization signal comprises the step of tuning the filter to a frequency of the authorization signal for removal of the authorization signal from the combined signal.

19. The method of claim 18 wherein the step of tuning the filter comprises the steps of:

providing an authorization key to the computer, the authorization key including information regarding the unique identifying characteristic of the device;

altering the filter in accordance with the information contained within the authorization key.

20. The method of claim 17 wherein the authorization signal is an analog signal.

* * * * *